United States Patent
Farai

(10) Patent No.: US 9,095,257 B2
(45) Date of Patent: *Aug. 4, 2015

(54) SYSTEMS AND METHODS FOR DETECTING ISCHEMIC EVENTS

(71) Applicant: Pacesetter, Inc., Sunnyvale, CA (US)

(72) Inventor: Taraneh Ghaffari Farai, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/069,197

(22) Filed: Oct. 31, 2013

(65) Prior Publication Data

US 2014/0058278 A1 Feb. 27, 2014

Related U.S. Application Data

(63) Continuation of application No. 12/039,626, filed on Feb. 28, 2008, now Pat. No. 8,600,503, which is a continuation of application No. 11/061,008, filed on Feb. 17, 2005, now abandoned, which is a continuation-in-part of application No. 10/652,443, filed on Aug. 28, 2003, now abandoned.

(51) Int. Cl.

| A61N 1/362 | (2006.01) |
| A61B 5/0452 | (2006.01) |
| A61B 5/0468 | (2006.01) |
| A61B 5/02 | (2006.01) |
| A61B 5/00 | (2006.01) |
| A61B 5/024 | (2006.01) |
| A61N 1/365 | (2006.01) |
| A61N 1/39 | (2006.01) |
| A61N 1/36 | (2006.01) |
| A61B 5/042 | (2006.01) |
| A61B 5/053 | (2006.01) |
| A61B 5/11 | (2006.01) |

(52) U.S. Cl.
CPC ......... *A61B 5/02028* (2013.01); *A61B 5/02405* (2013.01); *A61B 5/0468* (2013.01); *A61B 5/4836* (2013.01); *A61B 5/686* (2013.01); *A61B 5/7275* (2013.01); *A61B 5/7278* (2013.01); *A61B 5/7282* (2013.01); *A61B 5/742* (2013.01); *A61B 5/746* (2013.01); *A61N 1/3627* (2013.01); *A61N 1/36592* (2013.01); *A61B 5/042* (2013.01); *A61B 5/0538* (2013.01); *A61B 5/1118* (2013.01); *A61N 1/36114* (2013.01); *A61N 1/3962* (2013.01)

(58) Field of Classification Search
None
See application file for complete search history.

(56) References Cited

U.S. PATENT DOCUMENTS

| 4,798,211 | A | 1/1989 | Goor |
| 4,877,035 | A | 10/1989 | Bogen |
| 5,042,497 | A | 8/1991 | Shapland |
| 5,203,326 | A | 4/1993 | Collins |
| 5,330,507 | A | 7/1994 | Schwartz |
| 5,733,312 | A | 3/1998 | Schloss |
| 6,058,328 | A | 5/2000 | Levine |
| 6,381,493 | B1 | 4/2002 | Stadler |
| 6,442,420 | B1 | 8/2002 | Julu |
| 6,487,442 | B1 | 11/2002 | Wood |
| 6,609,023 | B1 | 8/2003 | Fischell |
| 6,922,585 | B2 | 7/2005 | Zhou |
| 7,079,887 | B2 | 7/2006 | Burnes |
| 7,181,277 | B1 | 2/2007 | Shelchuk |
| 7,181,282 | B1 * | 2/2007 | Province et al. ................ 607/17 |
| 7,254,440 | B1 * | 8/2007 | Kroll ............................. 600/517 |
| 7,702,391 | B1 * | 4/2010 | Farazi et al. ................... 607/25 |
| 7,869,870 | B1 | 1/2011 | Farazi |
| 8,145,309 | B2 | 3/2012 | Farazi et al. |
| 8,204,592 | B1 * | 6/2012 | Ostrow et al. .................. 607/14 |
| 2002/0065473 | A1 | 5/2002 | Wang |
| 2002/0188170 | A1 | 12/2002 | Santamore |
| 2003/0171782 | A1 | 9/2003 | Florio |
| 2003/0191403 | A1 | 10/2003 | Zhou |
| 2004/0122478 | A1 | 6/2004 | Standler |
| 2004/0186525 | A1 * | 9/2004 | Burnes et al. .................. 607/17 |
| 2004/0215090 | A1 | 10/2004 | Erkkila |
| 2006/0094967 | A1 | 5/2006 | Bennett |

FOREIGN PATENT DOCUMENTS

WO 03086187 A1 10/2003

OTHER PUBLICATIONS

Barthel et al., "Risk Stratification After Acute Myocardial Infarction b Heart Rate Turbulence," Circulation, 2003; 108: 1221, 11 pages.
Berkowitsch et al., "Prognostic Significance of Heart-Rate Tubulence in ICD Patients with DCM," the XIIth World Congress on 102431, Publishing ID; 396, 1 page.

(Continued)

*Primary Examiner* — Brian T Gedeon
(74) *Attorney, Agent, or Firm* — Theresa A. Raymer

(57) ABSTRACT

Embodiments of the present invention relate to implantable systems, and method for use therein, that can detect myocardial ischemic events. In accordance with specific embodiments of the present invention, short-term fluctuations in cardiac intervals that follow premature ventricular contractions (PVCs) are monitored. This allows myocardial ischemic events to be detected based on these monitored fluctuations. The cardiac intervals for which fluctuations are being monitored can be, for example, RR intervals. Alternatively, or additionally, short-term fluctuations in other types of cardiac intervals may be monitored. Such other cardiac intervals include, for example, PR intervals, PP intervals, QT intervals and RT intervals.

20 Claims, 5 Drawing Sheets

(56) References Cited

OTHER PUBLICATIONS

Bonnemeier et al., "Reflex Cardiac Activity in Ischemia and Reperfusion Heart Rate Turbulence in Patients Undergoing Direct Percutaneous Coronary Intervention for Acute Myocardial Infarction," Circulation, 2003; 108:958-964.
Cygankiewicz et al., "Heart Rate Turbulence Predicts Cardiac Death in Patients Undergoing CABG Surgery," Abstract ID: 102431, Publishing ID: 396, 1 page.
Davies et al., "Relation of Heart Rate and Blood Pressure Turbulence Following Premature Ventricular Complexes to Baroreflex Sensitivity in Chronic Congestive Heart Failure," The American Journal of Cardiology, vol. 87, Mar. 15, 2001, pp. 737-742.
Guzik et al., "A Phenomenon of Heart-Rate Turbulence, its Evaluation, and Prognostic Value," Card Eelctrophysiol Rev Sep. 2002; 6(3): 256-61.
"Heart Rate Turbulence Calculation," Technische Universitat Munchen. 2 pages.
Heart Rate Turbulence HRTIView, Technische Universitate Munchen, 2 pages.
Jeron et al., "Association of the Heart Rate Turbulence with Classic Risk Stratification Parameters in Postmyocardial Infarction Patients," A.N.E., Oct. 2003, vol. 8, No. 4, pp. 296-301.
Lin et al., "A Phenomenology Model of Normal Sinus Rhytm in Healthy Humans." IEEE Trans Biomed Eng Feb. 2002; 49(2): 97-109.
Lin et al., "Tight Mechanism Correlation Between Heart Turbulence and Baroreflex Sensitivity: Sequential Autonomic Blockade Analysis," J Cariovase Electrophysiol May 2002; 13(5): 427-31.
Lindgren et al., "Heart Rate Turbulence After Ventrical and Atrial Premature Beats in Subjects Without Structural Heart Disease," Abstract, Journal of Cardiovascular Electrophysiology, vol. 14, Issue 5, p. 447, May 2003.
Malik et al., "Heart Rate Turbulence," G Ital Cariol, vol. 29, Suppl 5, 1999, 5 pages.
Mrowka et al., "Blunted Arterial Baroreflex Causes"Pathological" Heart Rate Turbulence," Am J Physiol Regulatory Integrative Comp Physiol 279:R1171-R1175, Issue 4, Oct. 2000, 9 pages.
Schmidt et al. "Heart-Rate Turbulence After Ventricular Premature Beats as a Predictor for Mortality After Acute Myocardial Infarction," The Lancet, vol. 353, Apr. 24, 1999, pp. 130-1396 (6 pages).
Schwab et al., "Influence of the point of origin on heart rate turbulence after stimulation ventricular and atrial premature beats," Bsic Res Cardiol., 2004, 99:56-60.
Vikman et al., "Heart Rate Turbulence After Atrial Premature Beats Before Spontaneous Onset of Atrial Fibriliation," Journal of the American College of Cardiology, 2005: 45(2): 278-284.
Wantabe et al., "Effects of Ventricular Premature Stimulus Coupling Interval on Blood Pressure and Heart Rate Turbulence," Circulation, 2002; 106:325-330.
Wichterle et al., "Mechanisms Involved in Heart Rate Turbulence," Cardiac Electrophysiology Review Sep. 2002; 6 (3)262-266.
Wichterle et al., "Turbulence Slope After Atrial Premature Complexes is Significant Mortality Predictor in Patients After Myocardial Infarction," Abstract: 814-4, Citation: Supplement to Journal of the American College of Cardiology, Mar. 19, 2003, vol. 41, Issue 6 Suppl. A, 2 pages.
Advisory Action Mailed Dec. 19, 2007; Related U.S. Appl. No. 11/061,008.
Amendment filed Nov. 28, 2007; Related U.S. Appl. No. 11/061,008.
Final Office Action Mailed Sep. 28, 2007: Related U.S. Appl. No. 11/061,008.
Amendment filed Jun. 27, 2007; Related U.S. Appl. No. 11/061,008.
Non-Final Office Action Mailed Mar. 27, 2007; Related U.S. Appl. No. 11/061,008.
Notice of Allowance Mailed Aug. 20, 2013; Related U.S. Appl. No. 12/039,626.
Amendment filed Aug. 14, 2013; Related U.S. Appl. No. 12/039,626.
Amendment after Board Decision Mailed Jul. 23, 2013; Related U.S. Appl. No. 12/039,626.
Amendment mailed Jun. 18, 2010; Related U.S. Appl. No. 12/039,626.
Patent Board Decision mailed May 23, 2013; Related U.S. Appl. No. 12/039,626.
Examiners Answer mailed Mar. 14, 2011; Related U.S. Appl. No. 12/039,626.
Appeal Brief Filed Dec. 16, 2010; Related U.S. Appl. No. 12/039,626.
Notice of Appeal Filed Aug. 16, 2010; Related U.S. Appl. No. 12/039,626.
Advisory Action mailed Jul. 7, 2010; Related U.S. Appl. No. 12/039,626.
Non-Final Office Action Mailed May 6, 2008; Related U.S. Appl. No. 11/426,475.
Amendment filed May 29, 2009; Related U.S. Appl. No. 11/265,704.
Non-Final Office Action Mailed Jan. 31, 2011; Related U.S. Appl. No. 10/652,443.
Amendment filed Jul. 12, 2010; Related U.S. Appl. No. 10/652,443.
Non-Final Office Action mailed Mar. 10, 2010; Related U.S. Appl. No. 10/652,443.
Amendment filed Sep. 9, 2009; Related U.S. Appl. No. 10/652,443.
Non-Final Office Action Mailed Jun. 10, 2009, Related U.S. Appl. No. 10/652,443.
Amendment filed Mar. 5, 2009; Related U.S. Appl. No. 10/652,443.
Non-Final Office Action Mailed Dec. 5, 2008; Related U.S. Appl. No. 10/652,443.
Amendment filed Jun. 26, 2008; Related U.S. Appl. No. 10/652,443.
Non-Final Office Action Mailed Feb. 26, 2008; Related U.S. Appl. No. 10/652,443.
Advisory Action Mailed Jul. 11, 2007; Related U.S. Appl. No. 10/652,443.
Amendment filed Apr. 2, 2007; Related U.S. Appl. No. 10/652,443.
Final Office Action Mailed Feb. 27, 2007; Related U.S. Appl. No. 10/652,443.
Amendment filed Jul. 21, 2006, Related U.S. Appl. No. 10/652,443.
Amendment filed Jan. 4, 2006; Related U.S. Appl. No. 10/652,443.
Non-Final Office Action Mailed Oct. 4, 2005; Related U.S. Appl. No. 10/652,443.
Notice of Allowance Mailed Jun. 19, 2009; Related U.S. Appl. No. 11/181,719.
Notice of Allowance, Related U.S. Appl. No. 10/861,747.
Patent Board Decision—Examiner Reversed; Related U.S. Appl. No. 10/861,747.
Examiners Answer; Related U.S. Appl. No. 10/861,747.
Appeal Brief filed May 19, 2008; Related U.S. Appl. No. 10/861,747.
Pre-Brief Appeal Conference Decision, Related U.S. Appl. No. 10/861,747.
Notice of Appeal Mailed Jan. 17, 2008; Related U.S. Appl. No. 10/861,747.
Final Office Action Mailed Oct. 17, 2007; Related U.S. Appl. No. 10/861,747.
Amendment filed Jul. 30, 2007; Related U.S. Appl. No. 10/861,747.
Non-Final Office Action Mailed Mar. 28, 2007; Related U.S. Appl. No. 10/861,747.
Non-Final Office Action Mailed Mar. 17, 2009; Related U.S. Appl. No. 11/181,719.
Amendment filed Jan. 16, 2007; Related U.S. Appl. No. 10/861,747.
Non-Final Office Action Mailed Sep. 13, 2006; Related U.S. Appl. No. 10/861,747.
Non-Final Office Action Mailed Aug. 5, 2008; Related U.S. Appl. No. 11/181,719.
Bauer, "Heart Rate Turbulence," J Electrocardiaol 2003, 36 Suppl: 89-93, 1 page.
Bauer et al., "Dynamics of Heart Rate Turbulence Predicts Mortality After Acute Myocardial Infartion," 1 page.

* cited by examiner

SYSTEMS AND METHODS FOR DETECTING ISCHEMIC EVENTS

PRIORITY CLAIM

This application is a Continuation of application Ser. No. 12/039,626, filed Feb. 28, 2008, which is a continuation of U.S. patent application Ser. No. 11/061,008, entitled "System and Methods for Detecting Ischemic Events," filed Feb. 17, 2005, now abandoned, and a continuation-in-part of U.S. patent application Ser. No. 10/652,443, entitled "Implantable Cardiac Stimulation Device and Method that Measures Vagal Tone and Provides Responding Therapy," filed Aug. 28, 2003, now abandoned. The present invention relates to the commonly invented and commonly assigned applications, U.S. patent application Ser. No. 10/861,747, entitled "System and Method for Using Vagal Stimulation to Assess Autonomic Tone and Risk of Sudden Cardiac Death in an Implantable Cardiac Device," filed Jun. 4, 2004, now U.S. Pat. No. 7,869,870. Each of the aforementioned patent applications is incorporated here by reference in its entirety to provide continuity of disclosure.

FIELD OF THE INVENTION

The present invention relates generally to implantable systems and methods for detecting ischemic events.

BACKGROUND

Myocardial ischemia, which involves oxygen starvation of the myocardium, can lead to myocardial infarction and/or the onset of malignant arrhythmias if the oxygen starvation is not alleviated. Although myocardial ischemia is sometimes associated with the symptom of angina pectoris (i.e., chest pain), the majority of episodes of myocardial ischemia are asymptomatic or "silent."

A wide range of therapies are known for the treatment of myocardial ischemia once it is detected, including surgical revascularization, neural stimulation and use of a variety of biologically active agents or compounds which can remove blood clots, reduce cardiac workload or improve cardiac circulation. However, accurate and rapid detection of myocardial ischemia is necessary in order to reduce the morbidity and mortality from this often silent but deadly condition. In other words, without knowledge of the condition, it cannot be treated. Accordingly, those in the cardiac field are always searching for new and/or improved ways to detect ischemic episodes.

BRIEF SUMMARY OF THE INVENTION

Embodiments of the present invention relate to implantable systems, and method for use therein, that can detect myocardial ischemic events. In accordance with embodiments of the present invention, short-term fluctuations in cardiac intervals that follow premature ventricular contractions (PVCs) are monitored. This allows myocardial ischemic events to be detected based on these monitored fluctuations.

In accordance with an embodiment of the present invention, the monitoring of short-term fluctuations in cardiac intervals that follow PVCs includes monitoring short-term fluctuations in RR intervals that follow PVCs. That is, the cardiac intervals for which fluctuations are being monitored can be RR intervals. Alternatively, or additionally, fluctuations in other types of cardiac intervals may be monitored. Such other cardiac intervals include, for example, PR intervals, PP intervals, QT intervals and RT intervals.

In accordance with embodiments of the present invention, a degree of the short-term fluctuations in cardiac intervals that follow PVCs is measured. This enables ischemic events to be identified when the measured degree exceeds a threshold. In preferred embodiments, ischemic events are identified when the measured degree deviates from a baseline by more than a threshold. Preferably, values of the degree of short-term fluctuations in cardiac intervals (following PVCs), from which a baseline is determined, are measured when a patient is at rest.

In accordance with specific embodiments of the present invention, the degree of short-term fluctuations in cardiac intervals that follow PVCs is a degree of heart rate turbulence (HRT). In such embodiments, ischemic events are identified when the degree of HRT crosses a corresponding threshold (in a direction indicative of a diminished degree of HRT), or preferably, ischemic events are identified when a degree of HRT deviates from a baseline by more than a threshold.

In accordance with embodiments of the present invention, information related to each ischemic event is stored. This can include storing timing and duration information for each ischemic event. Alternatively, or additionally, a patient and/or physician is alerted in response a myocardial ischemic event being detected. In other embodiments, ischemia therapy is triggered in response to detecting a myocardial ischemic event.

This description is not intended to be a complete description of, or limit the scope of, the invention. Other features, aspects, and objects of the invention can be obtained from a review of the specification, the figures, and the claims.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Exemplary ICD

Figure 1:
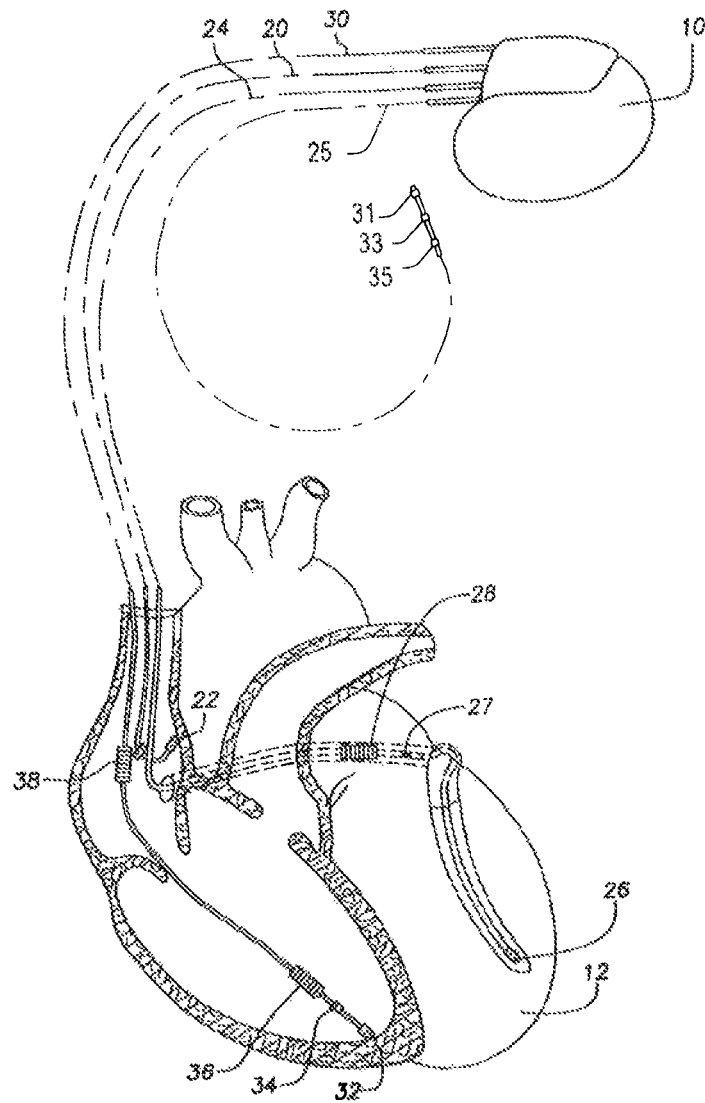
FIG. 1 is a simplified diagram illustrating an exemplary ICD in electrical communication with a patient's heart by means of three leads suitable for delivering multi-chamber stimulation and pacing therapy, and a fourth lead suitable for delivering vagal stimulation.
Figure 2:
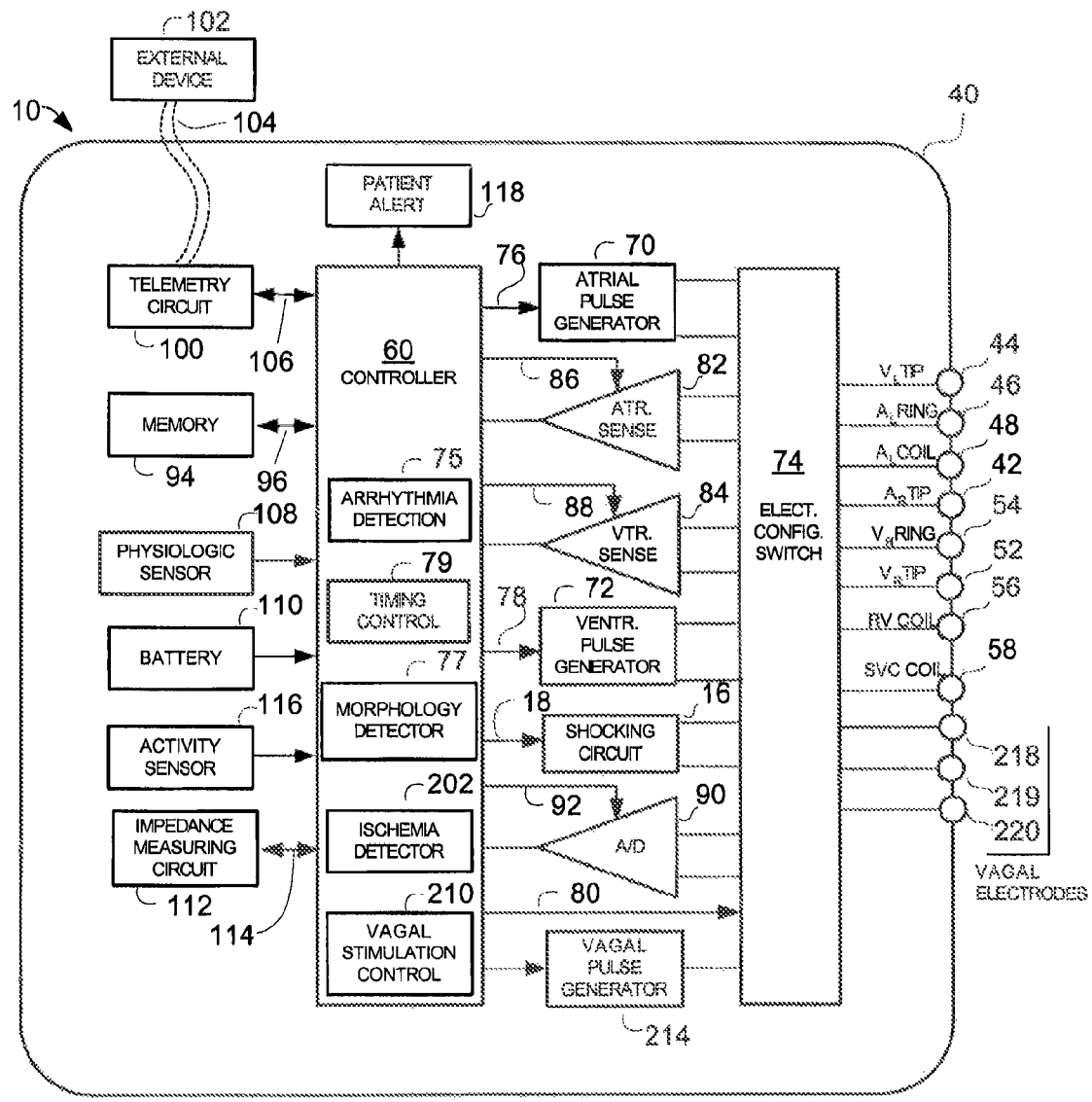
FIG. 2 is a functional block diagram of an exemplary ICD that can provide cardioversion, defibrillation, and pacing stimulation in four chambers of a heart, and detect ischemic events, in accordance with an embodiment of the present invention.

Before describing the invention in detail, it is helpful to describe an example environment in which the invention may be implemented. The present invention is particularly useful in the environment of an implantable cardiac device that can monitor electrical activity of a heart and deliver appropriate electrical therapy, for example, pacing pulses, cardioverting and defibrillator pulses, and drug therapy, as required. Implantable cardiac devices include, for example, pacemakers, cardioverters, defibrillators, implantable cardioverter defibrillators, and the like. The term "implantable cardiac device" or simply "ICD" is used herein to refer to any implantable cardiac device. FIGS. 1 and 2 illustrate such an environment in which embodiments of the present invention can be used.

Referring first to FIG. 1, an exemplary ICD 10 is shown in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle.

In FIG. 1, ICD 10 is also shown as being in electrical communication with the patient's heart 12 by way of a vagal stimulation lead 25, having, e.g., three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219 and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector is also shown as including vagal lead terminals (VAGAL ELECTRODES) 218, 219, and 220, which are configured for connection to vagal stimulation electrodes 31, 33, and 35, respectively, to support the delivery of vagal stimulation bursts.

At the core of ICD 10 is a programmable microcontroller 60, which controls the various modes of stimulation therapy. As is well known in the art, microcontroller 60 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the ICD's and their inter-relationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Also shown in FIG. 2, is a vagal pulse generator 214 that is controlled by vagal stimulation control 210 (within microcontroller 60) via a control signal 212, to trigger or inhibit the delivery of vagal stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detector 75 and morphology detector 77 to recognize and classify arrhythmia so that appropriate therapy can be delivered. The morphology detector 77 may also be used to detect signal morphologies that are useful for detecting ischemic events, in accordance with embodiments of the present invention described below. The arrhythmia detector 75 and morphology detector 77 can be implemented within the microcontroller 60, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

The operating parameters of ICD 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, Ill et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

Also shown in FIG. 2 is an activity sensor 116. The activity sensor 116 (e.g., an accelerometer) can be used to determine the activity of the patient. Such information can be used for rate responsive pacing, or, in accordance with embodiments of the present invention, to determine whether the patient is sufficiently at rest such that certain baseline measurements can be obtained. If the sensor 116 is a multi-dimensional accelerometer, then posture information can also be extracted. The following patents, which are incorporated herein by reference, describe exemplary activity sensors that can be used to detect activity of a patient (some also detect posture) U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." Simple activity sensors employ a piezoelectric crystal or a cantilever beam having a film of a piezoelectric polymer adhered to a surface of the beam. These are just a few exemplary types of activity sensors 116, which are not meant to be limiting.

The ICD 10 may also include a magnet detection circuitry (not shown), coupled to microcontroller 60. It is the purpose of the magnet detection circuitry to detect when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 can have an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38), As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2.

In accordance with an embodiment of the present invention, microcontroller 60 includes an ischemia detector 202, which as described in more detail below, can detect ischemic events based on monitored short-term fluctuations in cardiac intervals that follow premature ventricular contractions. The ischemia detector 202 can be implemented within the microcontroller 60, as shown in FIG. 2. Thus, this detector can be implemented by software, firmware, or combinations thereof. It is also possible that all, or portions, of ischemia detector 202 can be implemented using hardware.

In an embodiment, ischemia detector 202 triggers data acquisition circuit 90 and timing control circuit 79 to record cardiac intervals preceding and following intrinsic, induced or simulated premature ventricular contractions. Ischemia detector 202 measures, e.g., a degree of oscillatory behavior in the recorded cardiac intervals in order to assess autonomic tone, and by monitoring changes in the degree of oscillatory behavior, it determines whether a patient is experiencing a myocardial ischemic event. Ischemia detector 202 can also trigger ICD 10 to respond appropriately when a myocardial ischemic event is detected, as will be explained in more detail below. Additionally, in conjunction with a telemetry circuit 100, ischemia detector 202 can be configured to deliver status information, relating to the patient's ischemic events, to external device 102 through an established communication link 104. Ischemia detector 202 may also trigger a patient or physician alert in response to detecting a myocardial ischemic event. For example, a patient alert 118, which produces a vibratory or auditory alert, may be triggered by the ischemia detector.

Detecting Episodes of Ischemia

It is known that a ventricular premature beat (VPB) triggers fluctuations in cardiac cycle duration and a brief disturbance to arterial blood pressure. Such fluctuations have been referred to as heart rate turbulence (HRT) by Schmidt et al., in an article entitled "Heart-rate turbulence after ventricular premature beats as a predictor of mortality after acute myocardial infarction," *The Lancet*, Vol. 353: Pages 1390-96 (1999). In this article, Schmidt at al. define HRT as a characteristic initial acceleration and subsequent deceleration of sinus rhythm after a single VPB. The study by Schmidt et al, shows that the degree of HRT following a VPB can predict a patient's risk of sudden cardiac death (SCD). More specifically, it has been found that HRT is absent in the sinus rhythm of a patient at high-risk of SCD, but is present in the sinus rhythm of a patient at low-risk. Schmidt at al. also defined two parameters that can be used to quantify the degree of HRT following a VPB. One of the parameters, HRT onset, quantifies the initial acceleration of sinus rhythm after a single VPB. Another parameter, HRT slope, quantifies the speed of the subsequent deceleration of sinus rhythm after a single VPB. A further parameter, referred to as HRT is defined in an article by Watanabe et al., entitled "Effects of ventricular premature stimulus coupling interval on blood pressure and heart rate turbulence," *Circulation*, Vol. 106: Pages 325-330 (2002). In this article, Watanabe at al, define HRT timing as the first beat number of a five-beat RR sequence having the maximum regression slope.

Depression of baroreflex sensitivity (BRS) in the acute phase as well as the chronic phase of myocardial infarction (MI) has been shown, though the mechanism is not well understood. This impairment in BRS leads to a lack of appropriate baroreflex activity in response to a hypotensive stimulus, such as premature ventricular contraction (PVC), as demonstrated by a blunted HRT, a surrogate marker for BRS. ("Reflex Cardiac Activity in Ischemia and Reperfusion: Heart Rate Turbulence in Patients Undergoing Direct Percutaneous Coronary Intervention for Acute Myocardial Infarction." Bonnemeier et al, *Circulation*, Vol. 108: Pages 958-964 (2003)). Furthermore, in the acute phase of an MI, this impairment is shown to be restored within minutes after successful reperfusion by percutaneous coronary intervention (PCI).

The inventor of the present invention has realized that the same temporary impairment of baroreflex sensitivity (BRS), which occurs during an acute or chronic phase of MI, also occurs during ischemic episodes that are followed by reperfusion. The inventor of the present invention has further realized that this kind of temporary BRS deficiency makes monitoring short-term fluctuations in sinus cycle length (and other cardiac intervals) that follow premature ventricular contractions a good tool for monitoring myocardial ischemia. This will be discussed in more detail below.

Figure 3A:
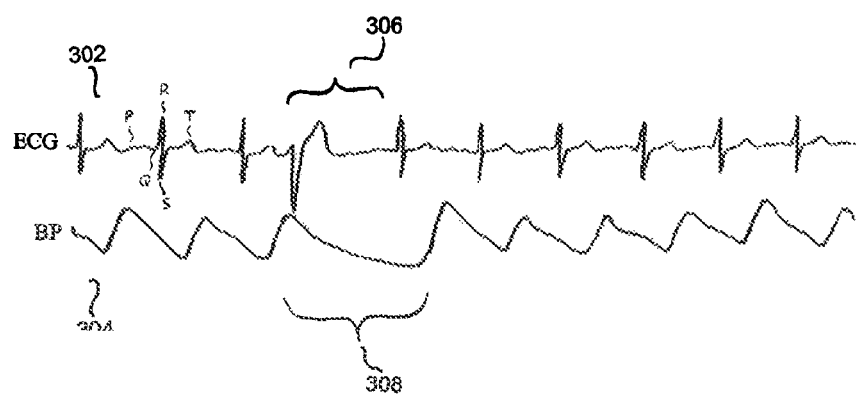
FIG. 3A illustrates an electrocardiogram (EGG) showing a PVC and a resulting disturbance in arterial blood pressure (BP).

FIG. 3A, which includes an ECG trace 302 and a blood pressure trace 304, can be used to show how a premature ventricular contraction (PVC), triggered by an intrinsic or paced (i.e., artificially induced) ventricular premature beat (VPB), causes a brief disturbance to arterial blood pressure. As can be appreciated from FIG. 3A, each cycle of the ECG waveform 302, which corresponds to a heart beat, includes a P wave that is a normally small positive wave caused by the beginning of a heart beat. Following the P wave there is a portion which is substantially constant in amplitude. The QRS complex of the ECG then normally occurs after the substantially constant portion, beginning with a Q wave that is normally a small negative deflection, which is then immediately succeeded by the R wave that is a rapid positive deflection. Following the R wave, the QRS complex is completed with an S wave that is generally characterized by a small positive inflection in the ECG signal. Following the S wave is a T wave, which is separated from the S wave by the ST segment. Various types of cardiac intervals (period of time between any two designated cardiac events) can be measured from an ECG signal. For example: an RR interval is the interval between successive R waves; a PP interval is the interval between successive P waves; a PR interval is the interval between a P wave and an R wave within the same beat; a QT interval is the interval between a Q wave and a T wave within the same beat; and an RT interval is the interval between an R wave and a T wave within the same beat. These are just a few examples of cardiac intervals that can be measured.

A premature ventricular contraction (PVC) is shown within the exemplary ECG trace 302. Also shown is the resulting disturbance 308 in the arterial blood pressure trace 304. Such an arterial blood pressure disturbance 308 can also be triggered by stimulating the vagus nerve, as was disclosed in commonly invented and assigned U.S. patent application Ser. No. 10/861,747, which was incorporated herein by reference above. As explained in the '747 application, a short burst of stimulation to the vagus nerve induces a drop in atrial pressure, which simulates a patient's cardiovascular response to a PVC. Accordingly, such stimulation of the vagus nerve will often be referred to hereafter as "simulating" a PVC.

Figure 3B:
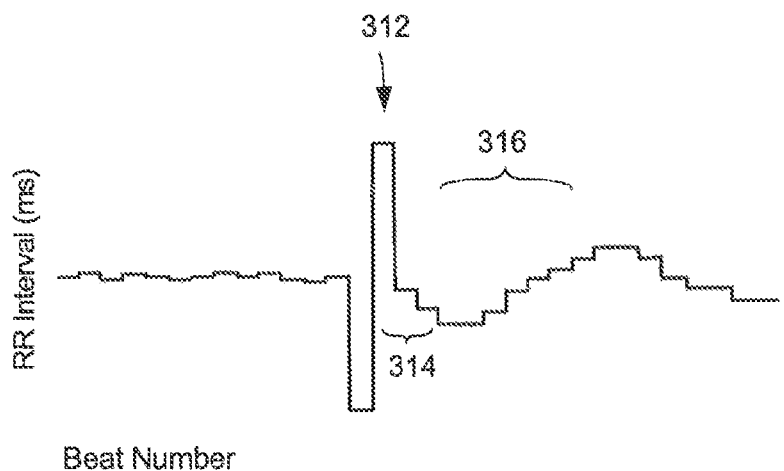
FIG. 3B illustrates the resulting fluctuation in sinus cycle lengths in response to a PVC, while a patient is not experiencing an episode of ischemia.
Figure 3C:
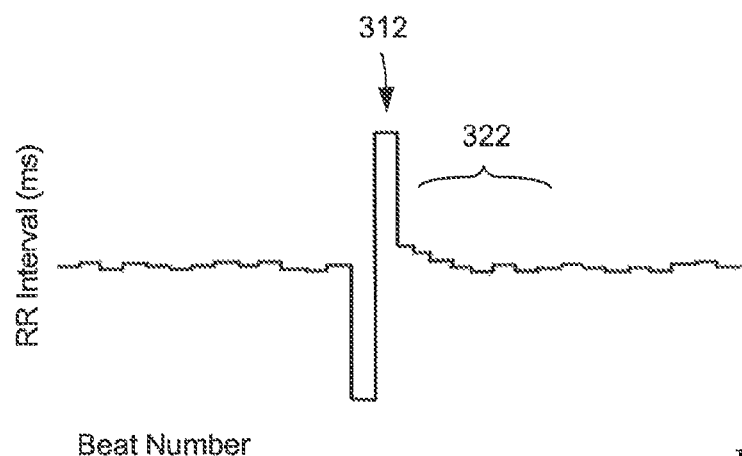
FIG. 3C illustrates the resulting fluctuation in sinus cycle lengths in response to a PVC, while a patient is experiencing an episode of ischemia.

FIGS. 3B and 3C are graphs of successive cardiac beats (horizontal axis) versus RR intervals (vertical axis), which are useful for determining the short-term fluctuation in RR intervals following a PVC. More specifically, FIG. 3B illustrates the resulting short-term fluctuation in sinus cycle lengths (i.e., RR intervals) following a PVC (e.g., PVC 306) when a patient is not experiencing an episode of myocardial ischemia. In contrast, the resulting fluctuation in cardiac intervals (RR intervals, in this example) following a PVC when the patient is experiencing an episode of myocardial ischemia, is shown in FIG. 3C. As can be seen in both FIGS. 3B and 3C, a PVC can be recognized by the compensatory pause 312 in sinus cycle length. Following this pause 312, there is a pronounced and recognizable fluctuation in RR intervals in response to the PVC, when the patient is not experiencing an episode of myocardial ischemia, as shown in FIG. 3B. This pronounced fluctuation includes both an initial acceleration 314 and a subsequent deceleration 316 following the PVC. In contrast, during a myocardial ischemic event, there is a negligible fluctuation 322 in RR intervals in response to a PVC, as shown in FIG. 3C. This negligible fluctuation 322 can also be referred to as a blunted response. Using the terminology of Schmidt et al, the degree of HRT is much greater when a patient is not experiencing a myocardial ischemic event, in comparison to when the patient is experiencing a myocardial ischemic event.

Figure 4:
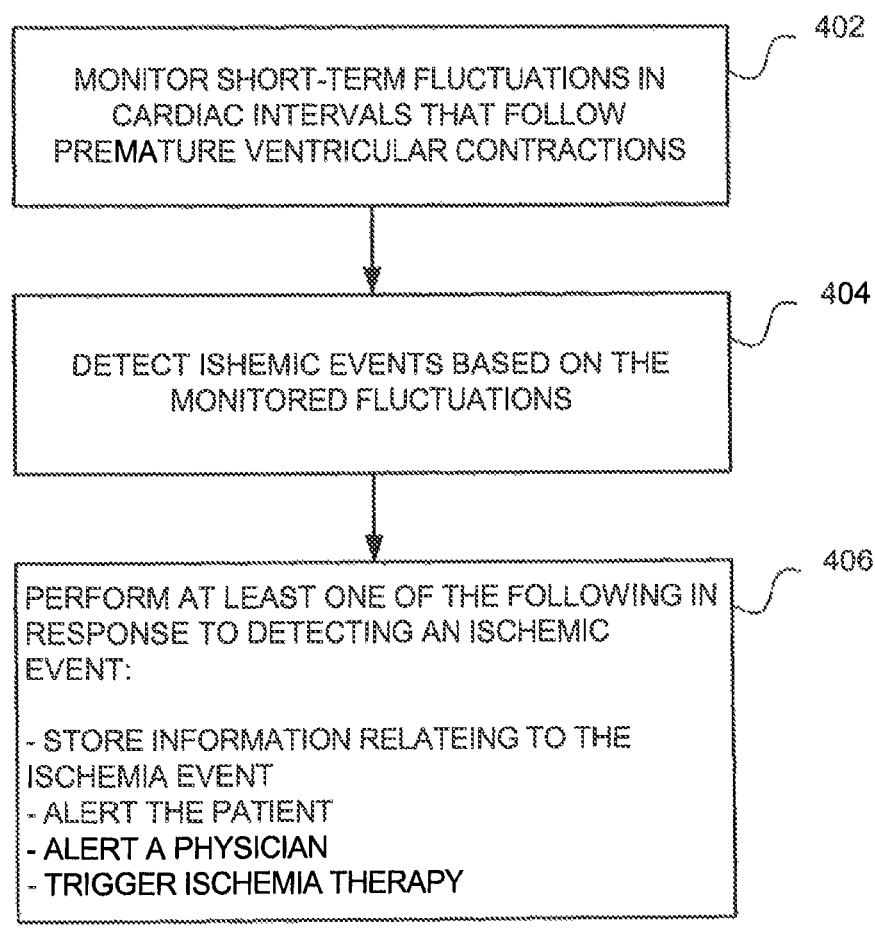
FIG. 4 is a high-level process flowchart that is useful for describing various embodiments of the present invention.

The flow diagram of FIG. 4 will now be used to describe how short-term fluctuations in cardiac intervals that follow premature ventricular contractions (also referred to as premature ventricular events or PVCs) are monitored to detect myocardial ischemic events (e.g., an episode of myocardial ischemia), in accordance with embodiments of the present invention. As shown in FIG. 4, at step 402, short-term fluctuations in cardiac intervals that follow PVCs are monitored. Such PVCs can be intrinsic, induced, or simulated. An intrinsic PVC results from an intrinsic premature contraction in the ventricle. Inducing a PVC involves applying a single premature stimulus to the ventricle using a pulse generator (e.g., 72), as explained in more detail U.S. patent application Ser. No. 10/652,443. Simulating a PVC involves stimulating a patient's vague nerve for a duration that simulates the compensatory pause 312, shown in FIG. 3B (thereby triggering an intrinsic baroreflex response to a drop in blood pressure), as described in U.S. patent application Ser. No. 10/861,747, which was incorporated by reference above. It is also possible that a PVC results from an intrinsic or induced premature atrial contraction (PAC) that conducts through the AV node into the ventricles, thereby causing the ventricles to prematurely contract. Inducing a PAC (to thereby cause a PVC) involves applying a single premature stimulus to the atrium using a pulse generator (e.g., 70).

Any fluctuations (or lack thereof) in cardiac intervals that occur due to PVCs will typically be recognizable only during the first 25 beats following the PVCs. Thus, the phrase short-term, as used herein, generally refers to about the first 25 successive beats following a PVC, but can refer to even less than the first 25 successive beats (e.g., it can refer to as little as about the first 10 successive beats following a PVC). In other words, in accordance with an embodiment of the present invention, step 402 can be performed by monitoring fluctuations in cardiac intervals corresponding to the first N successive beats that follow PVCs, where N is an integer between 10 and 25. However, it is possible that N be another number, and/or that the cardiac intervals corresponding to some beats be excluded. It is also noted that step 402 may include monitoring cardiac intervals that both precede and follow each PVC, such that cardiac intervals that precede a PVC can be used in calculating the short-fluctuations in cardiac intervals that follow the PVC. That is, cardiac intervals corresponding to beats that occur prior to PVCs may also be monitored at step 402. This is discussed in more detail below.

Still referred to FIG. 4, at step 404, ischemic events are detected based on the monitored short-term fluctuations in cardiac intervals. Then, at step 406, one or more response can be triggered if a myocardial ischemic event is detected. Many of these responses are discussed in more detail below.

More generally, sinus rhythm response to a PVC is monitored (and likely recorded) at step 402, and at step 404 the sinus rhythm data is processed in order to measure a degree of oscillatory behavior in the cardiac intervals following the PVC. The premature ventricular contractions referred to in step 402 can be intrinsic, induced or simulated, or combinations thereof. In other words, some PVCs can be intrinsic, some can be induced, while others are simulated in the manner described above.

In accordance with a specific embodiment of the present invention, at step 402, a number of RR intervals following a PVC (and possible a number of RR intervals preceding the PVC) and are recorded for processing. The invention is not, however, limited to monitoring fluctuations in RR intervals. For example, as will be discussed in more detail below, the inventor of the present invention has determined that measures of PR intervals can be used in place of RR intervals (or to supplement measures of RR intervals). Based on the description herein, one skilled in the relevant art(s) will understand that the invention can be implemented by monitoring short-term fluctuations in sinus rhythm intervals other than RR intervals or PR intervals. For example, other cardiac intervals that can be monitored are PP intervals, RT intervals and/or QT intervals.

In accordance with certain embodiments, step 402 includes quantifying the short-term fluctuations, and more specifically quantifying a degree of the short-term fluctuations in cardiac intervals that follow premature ventricular contractions. In accordance with an embodiment, step 404 includes identifying periods, when the measured degree crosses a corresponding threshold (in a direction indicative of diminished short term fluctuations), as myocardial ischemic events. Such thresholding may work with many patients. However, for patients that have reduced fluctuations to begin with, this type of thresholding may result in a high percentage of false positives. Accordingly, to reduce false positives, a baseline can be determined, such that a myocardial ischemic event is identified (at step 404) when the measured degree of short-term fluctuations in cardiac intervals deviates from the baseline by more than a threshold. As will be appreciated from the following discussion, more than one baseline and threshold may be used.

It believed that fluctuations in RR intervals may be attenuated (i.e., blunted) at higher heart rates. Accordingly, in preferred embodiments of the present invention, values of the degree of short-term fluctuations in RR intervals (and/or other cardiac intervals), that are used to determine one or more baseline, are measured (and likely stored) while a patient is at rest. A determination of whether the patient is sufficiently at rest (such that baseline measurements can be made) can be based, e.g., on heart rate measurements, on information obtained from an activity sensor (e.g., 116), or the like.

One approach for determining one or more baseline is to perform each baseline measurement after a naturally occurring (i.e., intrinsic) PVC caused by a naturally occurring VPB. A disadvantage of this technique, however, is that it cannot be executed on-demand or at regular intervals.

Another approach for determining one or more baseline, when naturally occurring PVCs are absent, is to perform baseline measurements following an artificially induced PVC, This approach is discussed in U.S. patent application Ser. No. 10/861,747, which was incorporated herein by reference above. A potential disadvantage of this technique, however, is that artificially inducing PVCs may be arrhythmiagenic.

A further approach for determining one or more baseline is to perform baseline measurements following an artificial stimulation of a patient's vagus nerve in order to induce a drop in arterial blood pressure, which simulates the patient's cardiovascular response to a PVC. An advantage of this technique is that it can be executed on-demand or at regular intervals, and it not likely to cause an arrhythmia. In such an approach, the patient's vagus nerve is stimulated for a duration that simulates compensatory pause 312, shown in FIG. 3B, in order to trigger an intrinsic baroreflex response to a drop in blood pressure. This is described in detail in U.S. patent application Ser No. 10/861,747, which was incorporated by reference above, and has been discussed above. As mentioned above, this technique is referred to herein as simulating a PVC.

Still another approach for determining one or more baseline parameter is to measure such parameter(s) following an artificially induced premature atrial contraction (PAC). An advantage of this technique is that it can be executed on-demand or at regular intervals, and is not likely to cause an arrhythmia. In such an approach, the patient's right or left atrium is stimulated prematurely to artificially induce a PAC. The PAC will be conducted through the AV node into the ventricles, thereby causing the ventricles to prematurely contract.

Baseline measurements can be averaged to produce a baseline. However, one of ordinary skill in the art would understand that more complex algorithms can be used to calculate baselines, and thus, that the present invention should not be limited to averaging. Also, any averaging (or other algorithm) that is used may or may not be performed using ensemble methods (e.g., ensemble averaging). Further, a baseline is preferably updated from time to time (e.g., once a week, or once a month). Such updating can be in response to a certain amount of time passing since a last update, or in response to another specific event or events being detected.

In specific embodiments, step 402 includes measuring a degree of heart rate turbulence (HRT), and step 404 includes identifying ischemic events based on the measured degree of HRT. In such embodiments, step 404 preferably includes detecting ischemic events when the degree of HRT exceeds a baseline by more than a threshold amount. Alternatively, a myocardial ischemic event can be detected at step 404 when the degree of HRT simply crosses a corresponding threshold in a direction indicative of a diminished degree of HRT (i.e., without using a baseline). The HRT parameter(s) measured at step 402 can include, e.g., turbulence onset (TO), turbulence slope (TS) and/or turbulence timing (TT).

In accordance with specific embodiments of the present invention, when determining a degree of HRT, RR intervals for an M beat sequence for each of N PVCs (intrinsic, induced or simulated) are stored, with each PVC beat being the $n^{th}$ beat within the M beat sequence. After storing the RR intervals for N of such sequences, ensemble averaging of the N sequences (of M beats each) is performed, with the PVC lined up in the same location for each sequence. Then, one or more HRT parameter (e.g., TO, TS and/or TT) is calculated based on these ensemble averages.

Referring back to FIGS. 3B and 3C, TO quantifies the amount of initial acceleration 314. Schmidt et al, specifically define TO as the difference between the mean of the first two sinus RR intervals after a ventricular premature beat (VPB) and the last two sinus RR intervals before the VPB, divided by the mean of the last two sinus RR intervals before the VPB (thus, a measurement of TO is expressed as a percentage). It is however noted that one of ordinary skill in the art would understand the similar results can be obtained even if the definition of TO were slightly modified. For example, more than just the last two and first two RR intervals before and after a VPB can be considered (e.g., using the last three and first three RR intervals before and after a VPB may produce similar results). Accordingly, the term TO should not be limited to the strict definition provided by Schmidt et al., but rather, should also encompass equivalent measures.

Referring back to FIGS. 3B and 3C, TS quantifies the speed of subsequent deceleration 316. Schmidt at al, specifically define TS as the maximum positive slope of a regression line assessed over any five subsequent sinus-rhythm RR intervals within the first 20 sinus-rhythm intervals after a VPB (thus, a measurement of TS is expressed in ms per RR interval). It is however noted that one or ordinary skill in the art would understand that similar results can be obtained even if the definition of TS were slightly varied. Similar results may be produced, e.g., if the regression line were assessed over any N subsequent sinus-rhythm RR intervals within the first M sinus-rhythm intervals after a VPB, where N and M need not be exactly 5 and 20, respectively. Accordingly, the term TS should not be limited to the strict definition provided by Schmidt et al., but rather, should also encompass equivalent measures.

As mentioned above, Watanabe at al. define HRT timing (TT) as the first beat number of a five-beat RR sequence having the maximum regression slope. It is however noted that one or ordinary skill in the art would understand that similar results can be obtained even if the definition of TT were slightly varied. For example, similar results may be obtained using the first beat number of an N-beat RR sequence having the maximum regression slope, where N need not be exactly 5.

Since each HRT parameter (i.e., TS, TO and TT) is expressed in different units, if more than one HRT parameter is being monitored, then a degree of HRT can be calculated using an algorithm that appropriately weights the different types of parameters to produce a single value. An appropriate baseline and threshold can be determined in a similar manner. Alternatively, a multi-dimensional table (e.g., a truth table) can be used such that each different type of parameter has its own corresponding threshold, and preferably also its own corresponding baseline. The detection of a myocardial ischemic event can then be defined as desired. For example, it may be that a myocardial ischemic event is only identified when every measured HRT parameter crosses its corresponding threshold in a direction indicative of a diminished HRT (or exceeds its baseline by more than a corresponding threshold). For another example, it may be that a myocardial ischemic event is identified when at least one HRT parameter crosses its corresponding threshold in a direction indicative of a diminished HRT (or exceeds its baseline by more than a corresponding threshold).

In a manner similar to that described above, the baselines and/or thresholds stored in this table can be updated from time to time. Such combining of baseline measurements having different units, and/or the use of multi-dimensional tables also applies where the short-term fluctuations of other types of cardiac intervals (instead or in addition to RR interval) are being monitored.

It is believed that the blunting of short-term fluctuations in cardiac intervals that follow a PVC is primarily a vagally mediated phenomenon, Since the vagal nerve feeds the SA node as well as the AV node, in addition to affecting RR intervals, it is believed that myocardial ischemia will also affect PR intervals that follow a PVC. Accordingly, in accordance with embodiments of the present invention, rather than (or in addition to) monitoring RR intervals, PR intervals can be monitored for the purpose of monitoring short-term fluctuations in cardiac intervals that follow a PVC. In other words, PR intervals can be the cardiac intervals that are monitored at step 402. As with RR intervals, PR intervals that both precede and follow each premature ventricular contraction can be monitored, such that PR intervals that precede the ventricular event can be used in calculating the short-fluctuations in PR intervals that follow the premature ventricular contraction. These are just two examples of how cardiac intervals that can be monitored. However, the present invention need not be limited to using only RR intervals and/or PR intervals. This is because it is believed that short-term fluctuations in these other types of cardiac intervals will also be blunted, following PVCs. For example, short-term fluctuations in other types of cardiac intervals can be monitored, including, but are not limited to, PP, QT and RT intervals.

In accordance with specific embodiments of the present invention, step 402 is performed by monitoring short-term fluctuations in cardiac intervals that follow premature ventricular contractions (as can be appreciated from FIGS. 3B and 3C). However, it is noted that this may include monitoring cardiac intervals that both precede and follow each premature ventricular contraction, such that cardiac intervals that precede the premature ventricular event can be used in calculating the short-term fluctuations in cardiac intervals that follow the premature ventricular contraction. For example, as explained above, RR intervals that precede and follow a VPB are used to calculate turbulence onset (TO).

It is clear from the above description that the present invention is not limited to measuring HRT parameters following a premature ventricular event. Rather, based on the description herein, one skilled in the relevant art(s) will understand that the invention can be implemented by measuring other parameters that quantify the oscillatory behavior following a premature ventricular event and that also serve as surrogate measures of the level of vagal activity (e.g., mean magnitude, onset, and/or speed of RR, PR, PP, QT or RT acceleration or deceleration, the overall morphology of the RR, PR, PP, OT or RT oscillation, time course of the overall oscillation, etc.). More generally, embodiments of the present invention are useful for detecting episodes of myocardial ischemia based on the short-term fluctuations in cardiac intervals that follows an actual, induced or simulated premature ventricular contraction. This can be accomplished in any of the manners discussed above. It is also possible to monitor the overall morphology of the oscillations of RR, PR, (or other cardiac intervals) following PVCs. This can include comparing a monitored morphology to a baseline morphology, and detecting myocardial ischemic events when the monitored morphology differs from the baseline morphology by more than specified degree. A degree of similarity/difference between a monitored morphology and a baseline morphology can be accomplished, e.g., by determining a correlation between the two morphologies. Of course other techniques are also possible. As would be apparent from the above discussion, a baseline morphology is preferably based on measurements of cardiac intervals that correspond to premature ventricular contractions that occur while a patient is at rest.

If short-term fluctuations in more than one type of parameter (e.g., cardiac interval and/or HRT parameter) following PVCs are being monitored, then a degree of fluctuations can be calculated using an algorithm that appropriately weights the fluctuations corresponding to the different types parameters to produce a single value. An appropriate baseline and threshold can be determined in a similar manner. Alternatively, a multi-dimensional table (e.g., a truth table), or the like, can be used such that each different type of parameter (e.g., cardiac interval and/or HRT parameter) has its own corresponding threshold, and preferably also its own corresponding baseline. The detection of a myocardial ischemic event can then be defined as desired. For example, it may be that a myocardial ischemic event is only identified when all monitored parameters of short-term fluctuations appropriately cross their corresponding thresholds (or exceed their baselines by more than the corresponding thresholds). For another example, it may be that a myocardial ischemic event is identified when at least one monitored parameter crosses its corresponding threshold in the appropriate direction (or exceeds its baseline by more than a corresponding threshold). More generally, it may be that a myocardial ischemic event is identified when n out of m monitored parameters crosses its corresponding threshold in the appropriate direction (or exceeds its baseline by more than a corresponding threshold). Measures of morphology can also be used in combinations with other types of measurements. These are just a few examples of how measurements of different types of parameters can be used to detect ischemic events. One of ordinary skill in the art would appreciate from this description that other ways are also within the spirit and scope of the present invention.

As mentioned above, at step 406 one or more response can be triggered if a myocardial ischemic event is detected. In accordance with an embodiment of the present invention, information related to each ischemic event can be stored. This can include, for example, storing timing and duration information for each ischemic event and providing a measure of ischemia burden (which can basically be displayed with previously determined ischemia burdens from say month ago and compared to see improvement or worsening of cardiovascular condition). Such information can be continually, or from time to time, automatically uploaded to an external device (e.g., 102). Such an external monitoring device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

A myocardial infarction (i.e., a heart attack) is always preceded by a myocardial ischemic event. Thus, the detection of a myocardial ischemic event may be indicative of an immanent myocardial infarction. Accordingly, in an embodiment, a patient is alerted when a myocardial ischemic event is detected, thereby allowing the patient to respond appropriately. Such an alert could be a vibratory or auditory alert that originates from within an implantable device. Alternatively, an implantable device may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, a myocardial infarction may be avoided, or if it does occur, the patient will be less dangerous to themselves and others if the patient is resting when the infarction occurs (as opposed, e.g., to driving a car).

Additionally or alternatively, the patient can be instructed to take medication when alerted. In still another embodiment, a physician or other person (e.g., a caregiver, guardian or relative of the patient) is alerted whenever a myocardial ischemic event is detected.

In further embodiments, a myocardial ischemia therapy can be triggered in response to detecting an ischemic event. One type of therapy would be for an implanted device (e.g., device 10) to stimulate the vagal nerve, in an attempt to slow down the heart rate. In another embodiment, the implanted device, if appropriately equipped, can deliver an appropriate drug therapy. One of ordinary skill in the art would appreciate from the above description that other types of therapies can be triggered.

These are just a few examples of the types of responses that can be performed upon detection of a myocardial ischemic event. One of ordinary skill in the art would understand from the above description that other responses are also possible, while still being within the spirit and scope of the present invention.

As mentioned above, fluctuations in cardiac intervals may be normally attenuated (i.e., blunted) at higher heart rates. Accordingly, it may be beneficial to also monitor heart rate and or activity (using a single or multi-dimensional activity sensor) and to store such information together with timing and duration information for each detected ischemic event.

The above described embodiments of the present can be used to independently detect myocardial ischemic events, or can be used together with other techniques for detecting ischemic events. For example, the above described embodiments can be used to supplement (e.g., to increase the confidence level of) the detection of an ischemic event using some other technique. Alternatively, some other technique can be used to supplement the detection of an ischemic event that was detected using one of the above described embodiments of the present invention. For a more specific example, in U.S. Pat. No. 6,609,023 (Fishell et al.), which is incorporated herein by reference, ST segments are analyzed for the purpose of detecting myocardial infarctions and/or myocardial ischemia. More specifically, the '023 patent discloses that ischemia can be detected by comparing ST segment shifts to an appropriate threshold, where an "ST shift" is the difference between the ST deviation of any single beat in a recently collected electrogram segment and a baseline average ST deviation extracted from a baseline electrogram segment. This is just one example of a technique that can be used together with the embodiments of the present invention that detect ischemic events based on monitored short-term fluctuations in cardiac intervals that follow premature ventricular contractions. Other techniques can be used for supplementing embodiments of the present invention. Similarly, embodiments of the present invention can be used to supplement other techniques.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. An implantable system, comprising:
   a monitor that monitors short-term fluctuations in cardiac intervals that follow premature ventricular contractions;
   a detector that detects ischemic events based on the monitored fluctuations, determines whether a patient is experiencing an ischemic event, and, when the patient is experiencing an ischemic event, at least one of the following: triggers myocardial ischemia therapy, transmits an alert that an action appropriate to the detection of myocardial ischemia should be taken, and stores a measure of myocardial ischemia burden.

2. The system of claim 1, wherein the monitor monitors cardiac intervals that both precede and follow each premature ventricular contraction, such that cardiac intervals that precede the premature ventricular contraction can be used in calculating the short-term fluctuations in cardiac intervals that follow the premature ventricular contraction.

3. The system of claim 1, wherein the monitor monitors short-term fluctuations in cardiac intervals within beats that follow a premature ventricular contraction.

4. The system of claim 1, wherein the premature ventricular contractions are intrinsic, induced or simulated, or combinations thereof.

5. The system of claim 1, wherein the detector further:
   determines a degree of short-term fluctuations in cardiac intervals that follow premature ventricular contractions; and
   identifies ischemic events when the measured degree crosses a corresponding threshold in a specified direction.

6. The system of claim 1, wherein the detector further:
   determines a degree of short-term fluctuations in cardiac intervals that follow premature ventricular contractions; and
   identifies ischemic events when the measured degree deviates from a baseline by more than a threshold.

7. The system of claim 6, wherein the monitor monitors short-term fluctuations in cardiac intervals that follow premature ventricular contractions when a patient is at rest and after the patient is at rest, and wherein the detector further determines a baseline based on the values measured when the patient is at rest and determines whether a patient is experiencing an ischemic event based on a comparison of the baseline to the monitored short-term fluctuations in cardiac intervals that follow premature ventricular contractions after the patient is at rest.

8. The system of claim 7, wherein the monitor and detector update the baseline from time to time.

9. The system of claim 1, wherein the monitored fluctuations comprise a degree of heart rate turbulence (HRT), and wherein the detector identifying periods, when the degree of HRT crosses a corresponding threshold in a specified direction, as ischemic events.

10. The system of claim 1, wherein the monitored fluctuations comprise degree of heart rate turbulence (HRT), and wherein the detector identifying periods, when the degree of HRT deviates from a baseline by more than a threshold amount, as ischemic events.

11. The system of claim 10, wherein the monitored fluctuations comprise at least one HRT parameter measured when a patient is at rest; and wherein the detector determines the baseline based on the at least one HRT parameter measured when the patient is at rest.

12. The system of claim 10, wherein the monitor and detector update the baseline from time to time.

13. The system of claim 11, wherein the at least one HRT parameter comprises at least one of:
   turbulence onset (TO);
   turbulence slope (TS); and
   turbulence timing (TT).

14. The system of claim 1, wherein the detector triggers myocardial ischemia therapy when the patient is experiencing an ischemic event, and wherein the myocardial ischemia therapy comprises stimulating the vagal nerve, and wherein the system further comprises a vagal stimulation electrode that stimulates the vagal nerve when triggered by the detector.

15. An implantable system for detecting myocardial ischemic events, comprising:
   a monitor that monitors morphology of a signal that is indicative of cardiac intervals that follow premature ventricular contractions; and
   a detector that detects myocardial ischemic events based on the monitored morphology, determines whether a patient is experiencing an ischemic event, and when the patient is experiencing an ischemic event, at least one of the following: triggers myocardial ischemia therapy, transmits an alert that an action appropriate to the detection of myocardial ischemia should be taken, and stores a measure of myocardial ischemia burden.

16. The system of claim 15, wherein the detector compares the monitored morphology to a baseline morphology, and detects myocardial ischemic events when the monitored morphology differs from the baseline morphology by more than a specified degree.

17. The system of claim 15, wherein the baseline morphology is determined based on measurements of cardiac intervals that correspond to premature ventricular contractions that occur while a patient is at rest.

18. The system of claim 15, wherein the monitor monitors fluctuations in cardiac intervals corresponding to the first N successive beats that follow premature ventricular contractions, where N is an integer between 10 and 25.

19. The system of claim 15, further comprising:
a display that displays the present ischemia burden with previously determined ischemia burdens, wherein the detector further compares the present ischemia burden with the previously determined ischemia burdens, and determines whether a patient's cardiovascular condition has worsened or improved over a time period based on the comparison.

20. The system of claim 15, wherein the detector triggers myocardial ischemia therapy when the patient is experiencing an ischemic event, and wherein the myocardial ischemia therapy comprises stimulating the vagal nerve, and wherein the system further comprises a vagal stimulation electrode that stimulates the vagal nerve when triggered by the detector.

* * * * *

UNITED STATES PATENT AND TRADEMARK OFFICE
CERTIFICATE OF CORRECTION

| | | |
|---|---|---|
| PATENT NO. | : 9,095,257 B2 | Page 1 of 1 |
| APPLICATION NO. | : 14/069197 | |
| DATED | : August 4, 2015 | |
| INVENTOR(S) | : Taraneh Ghaffari Farazi | |

It is certified that error appears in the above-identified patent and that said Letters Patent is hereby corrected as shown below:

ON THE TITLE PAGE

Item (72), please delete "Taraneh Ghaffari Farai" and insert -- Taraneh Ghaffari Farazi --.

Signed and Sealed this
Sixteenth Day of February, 2016

Michelle K. Lee
*Director of the United States Patent and Trademark Office*